United States Patent [19]
Brown, deceased, et al.

[11] 3,960,943
[45] June 1, 1976

[54] N-CYCLOALKYLDITHIO-N'-FLUOROPHENYL UREAS

[75] Inventor: Melancthon S. Brown, deceased, late of Berkeley, Calif., by Gustave K. Kohn, special administrator; Gustave K. Kohn, Berkeley, Calif.

[73] Assignee: Chevron Research Company, San Francisco, Calif.

[22] Filed: Jan. 6, 1975

[21] Appl. No.: 538,829

Related U.S. Application Data

[63] Continuation-in-part of Ser. No. 526,494, Nov. 25, 1974, abandoned, which is a continuation-in-part of Ser. No. 250,907, May 8, 1972, Pat. No. 3,853,966, which is a continuation-in-part of Ser. Nos. 88,212, Nov. 9, 1970, Pat. No. 3,755,437, and Ser. No. 189,732, Oct. 15, 1971, abandoned.

[52] U.S. Cl................................ 260/453 R; 71/98; 260/553 A
[51] Int. Cl.².......................................... C07C 119/00
[58] Field of Search........ 260/553 A, 453 R, 545 R; 71/98, 120

[56] References Cited
UNITED STATES PATENTS

| | | | |
|---|---|---|---|
| 3,385,692 | 5/1968 | Knowles | 71/120 |
| 3,539,538 | 11/1970 | Behforouz | 260/780 |
| 3,812,209 | 5/1974 | Brown | 260/453 R |

*Primary Examiner*—Robert V. Hines
*Assistant Examiner*—Thomas A. Waltz
*Attorney, Agent, or Firm*—G. F. Magdeburger; Dix A. Newell; Raymond Owyang

[57] ABSTRACT

N-cycloalkyldithio-N'-fluorophenyl ureas are useful for eliminating grassy and broadleaf weeds selectively from crop plants such as corn, sorghum and potatoes. The ureas are prepared by reacting an N-clorothio-N'-fluorophenyl urea with a cycloalkyl mercaptan in the presence of an acid acceptor.

1 Claim, No Drawings

N-CYCLOALKYLDITHIO-N'-FLUOROPHENYL UREAS

RELATED APPLICATION

This application is a continuation-in-part of application Ser. No. 526,494, filed Nov. 25, 1974 now abandoned, which in turn is a continuation-in-part of application Ser. No. 250,907, filed May 8, 1972, now U.S. Pat. No. 3,853,966, which in turn is a continuation-in-part of appications Ser. No. 88,212, filed Nov. 9, 1970, now U.S. Pat. No. 3,755,437, and Ser. No. 189,732, filed Oct. 15, 1971, now abandoned, the disclosures of which applications are incorporated herein by reference.

DESCRIPTION OF THE PRIOR ART

N-hydrocarbyldithio-N'-aryl ureas are disclosed in U.S. Pat. No. 3,812,209.

DESCRIPTION OF THE INVENTION

The N-cycloalkyldithio-N'-fluorophenyl ureas of the invention are represented by the formula (III):

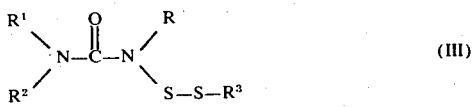

wherein R is alkyl of 1 to 6 carbon atoms, $R^1$ is hydrogen or alkyl of 1 to 6 carbon atoms, $R^2$ is fluorophenyl, and $R^3$ is cycloalkyl of 3 to 10 carbon atoms.

Representative alkyl groups which R and $R^1$ may represent include methyl, ethyl, n-propyl, isopropyl, n-butyl, t-butyl, n-pentyl and n-hexyl.

Representative cycloalkyl groups which $R^3$ may represent include cyclopropyl, cyclopentyl, cyclohexyl, 2-methylcyclohexyl, 4-methylcyclohexyl, cycloheptyl and cyclooctyl.

Preferably R is alkyl of 1 to 3 carbon atoms, especially methyl.

Preferably $R^1$ is hydrogen.

Preferably $R^2$ is 2-fluorophenyl.

Preferably $R^3$ is cycloalkyl of 5 to 6 carbon atoms, expecially cyclohexyl.

The ureas of the invention are prepared by reacting an N-chlorothio urea (I) with a cycloalkyl mercaptan of 3 to 10 carbon atoms, preferably 5 to 6 carbon atoms (II), as depicted in the following reaction (1):

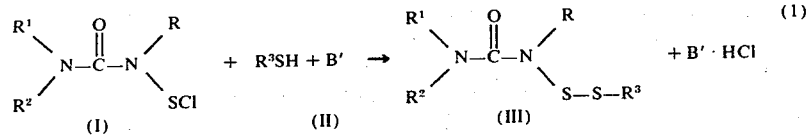

wherein R, $R^1$, $R^2$ and $R^3$ have the same significance as previously defined and B' is an acid acceptor.

The acid acceptor is an organic base, e.g., alkali metal hydroxide, bicarbonate or carbonate, or an organic nitrogen base having no N—H groups, such as a pyridine compound or a trialkylamine. Suitable pyridine compounds are pyridine and pyridine compounds of 6 to 10 carbon atoms and of 1 to 2 alkyl groups such as 2-methylpyridine, 2-ethylpyridine, 3-methylpyridine, 3,5-dimethylpyridine, and 2-butylpyridine. Suitable trialkylamines are those wherein the alkyl group contains individually 1 to 4 carbon atoms, such as trimethylamine, triethylamine, tripropylamine and tributylamine. The preferred acid acceptors are pyridine compounds, especially pyridine.

Reaction (1) is conducted in the liquid phase in an inert diluent, preferably the same inert diluents employed in the preparation of the N-chlorothio urea reactant (I), as hereinafter described. The preferred diluents are chlorinated hydrocarbons of 1 to 2 carbon atoms, such as methylene dichloride, chloroform, carbon tetrachloride and ethylene dichloride. Generally, the amount of diluent employed ranges from 1 to 50 mols per mol of N-chlorothio urea reactant.

The N-chlorothio urea reactant (I) and the mercaptan (II) are generally employed in substantially equimolar amounts, e.g., the molar ratio of the urea (I) to the mercaptan (II) generally varies from 1.5:1 to 1:1.5. The molar ratio of acid acceptor to N-chlorothio urea is also substantially equimolar, e.g., the molar ratio of acid acceptor to urea generally varies from 1.5:1 to 1:1.5.

Reaction (1) is suitably conducted at a temperature between −20°C. and the boiling point of the diluent, although temperatures between 0°C. and 50°C. are preferred. The reaction is conducted at or above atmospheric pressure.

The cycloalkyldithio urea product (III) is recovered by conventional procedures such as extraction, crystallization, chromatography, etc.

The N-chlorothio urea reactant (I) is prepared in accordance with the following reaction (2):

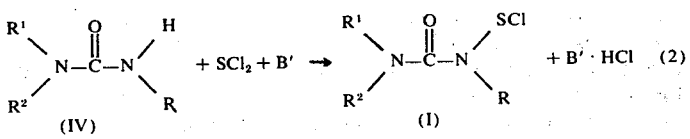

wherein R, $R^1$, $R^2$ and B' have the same significance as previously defined.

Generally, commercially available sulfur dichloride of reasonable purity, e.g., greater than 90–98% purity, is suitably employed. The sulfur dichloride may contain small amounts of an inhibitor such as tributylphosphate or triethylphosphate.

The sulfur dichloride and the urea (IV) are employed in substantially equimolar amounts, e.g., the molar ratio of sulfur dichloride to the urea compound generally varies from about 1.5:1 to 1:1.5, although molar ratios of sulfur dichloride to the urea compound of 1.4:1 to 1.1:1 are preferred. The molar ratios of acid acceptor to sulfur dichloride are also substantially equimolar, e.g., the molar ratio of acid acceptor to sulfur dichloride varies from about 1.5:1 to 1:1.5, although molar ratios of acid acceptor to sulfur dichloride of 1:1 to 1:1.2 are preferred.

In general, reaction (2) is accomplished by reacting the urea compound (IV) and the sulfur dichloride in the presence of the acid acceptor compound in the liquid phase in an inert diluent. The reaction is suitably conducted by adding the sulfur dichloride to a mixture of the urea and the acid acceptor in an inert diluent. Alternatively, the reaction is conducted by adding a mixture of the urea and acid acceptor to a solution of the sulfur dichloride in an inert diluent. Another method for conducting the reaction comprises reacting the urea and sulfur dichloride in the presence of a limited amount of free uncomplexed acid acceptor. This is suitably accomplished by the addition of the acid acceptor to a substantially equimolar mixture of the urea and the sulfur dichloride so that the mols of free acid acceptor to the total mols of urea reactant and N-chlorothio urea product is less than 0.2:1, preferably less than 0.1:1, and more preferably less than 0.05:1. In other words, during the course of the reaction between the sulfur dichloride and the urea reactant, there should be at least 5 mols of the urea reactant and the N-chlorothio urea product per mol of acid acceptor which is not complexed with hydrochloric acid. Provided that the reaction is conducted with the restricted amount of acid acceptor indicated above, the contacting of the acid acceptor with the mixture of the urea and the sulfur dichloride can be conducted by a variety of procedures. In one modification, the acid acceptor is added in increments, e.g., dropwise, in an inert diluent, if desired, to a mixture of the urea and sulfur dichloride in an inert diluent. In another modification, the acid acceptor is added continuously to a mixture of the urea and sulfur dichloride in an inert diluent.

Suitable inert diluents for reaction (2) include alkanes of 5 to 10 carbon atoms, such as hexane, isooctane and decane; aromatic compounds such as benzene and chlorobenzene, oxygenated hydrocarbons such as acyclic alkyl ethers, e.g., dimethoxyethane and dibutyl ether; and cycloalkyl ethers, e.g., dioxane, tetrahydrofuran and tetrahydropyran. Other suitable diluents include nitriles such as acetonitrile and propionitrile, dialkylamides such as dimethylformamide and dialkylsulfoxides such as dimethylsulfoxide. Preferred diluents are chlorinated hydrocarbons of 1 to 2 carbon atoms, such as methylene dichloride, chloroform, carbon tetrachloride and ethylene dichloride. Generally, the amount of diluent employed ranges from 1 to 50 mols per mol of N-chlorothio urea reactant.

Reaction (2) is suitably conducted at a temperature between −20°C. and the boiling point of the diluent, although temperatures between 0°C. and 50°C. are preferred. The reaction is conducted at or above atmospheric pressure.

The N-chlorothio urea is suitably isolated from the reaction mixture by conventional procedures such as extraction, distillation, chromatography, etc. Alternatively, a solution of the N-chlorothio urea in the reaction diluent, preferably after removal of the acid acceptor hydrochloride salt produced in the reaction, is reacted with the mercaptan (II) according to reaction (1) to produce the urea product (III) of the invention.

EXAMPLES

The preparation of the ureas of the invention is illustrated by the following examples.

EXAMPLE 1

Preparation of N-chlorothio-N-methyl-N'-(2-fluorophenyl) urea

A 5.7-g (0.055 mol) sample of sulfur dichloride was added dropwise to a mixture of 8.4 g (0.05 mol) N-methyl-N'-2-fluorophenyl urea and 4.7 g (0.06 mol) pyridine in 50 ml methylene chloride cooled in an ice bath. After the completion of the addition, the pyridine hydrochloride formed during the reaction was filtered. Hexane was added to the filtrate to precipitate additional pyridine hydrochloride, which was removed by filtration. Evaporation of the resulting filtrate gave a clear red oil. The nuclear magnetic resonance (NMR) spectrum of the oil showed an N-methyl singlet at 3.5 ppm (relative to tetramethylsilane).

Elemental analysis showed: %S, calc. 13.6, found 13.6; %Cl, calc. 15.1, found 15.4.

EXAMPLE 2

N-methyl-N-cyclohexyldithio-N'-(2-fluorophenyl) urea

A 55.4-g (0.73 mol) sample of pyridine was added dropwise to a slurry of 100 g (0.6 mol) N-methyl-N'-2-fluorophenyl) urea and 68.0 g (0.66 mol) sulfur dichloride in 600 ml methylene dichloride at 25°–30°C. After the addition was completed, the reaction mixture was stirred for about 5 minutes and filtered to give a solution of the chlorothio urea product in methylene dichloride. To the chlorothio urea solution was then added dropwise a solution of 62.8 (0.54 mol) cyclohexyl mercaptan and 47.4 g (0.6 mol) pyridine in 50 ml methylene dichloride at 0°C. After the addition was completed, the reaction mixture was stirred at about 0°C. for 20 minutes, washed with water, washed with sodium bicarbonate solution, dried over magnesium sulfate, filtered and evaporated under reduced pressure to give a yellow oil, which crystallized from hexane as a white solid. The solid product was recrystallized from hexane to give the urea product, m.p. 42.5°–43° C.

Elemental analysis for the product showed: %S, calc. 20.4, found 19.2; %N, calc. 8.9, found 9.2.

UTILITY

The cycloalkyldithio ureas are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed. The compounds are particularly effective for the selective control of broadleaf and grassy weeds in corn, sorghum and potato crops.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally for both pre- and post-emergent control, the herbicidal compounds of the invention are applied at rates of 0.2 to 60 kg/ha, and the preferred rate is in the range 0.5 to 40 kg/ha.

Pre- and post-emergent herbicidal tests on a representative compound of the invention and several structurally related N-dithio-substituted ureas were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 11 and 3.7 micrograms/cm$^2$ (1.01 and 0.34 lbs/acre). The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table I.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 11, 3.7 and 1.2 micrograms/cm$^2$ (1.01, 0.34 and 0.11 lbs/acre). After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

All compounds tested had the formula

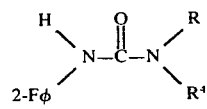

wherein $R^4$ is designated in the Tables and wherein R is methyl except for Compound No. 2, which is hydrogen.

TABLE I

Pre-Emergence

| No. | $R^4$ | Conc | Wild Oats (Avena fatua) | Water-grass (Echinochloa crusgalli) | Crabgrass (Digitaria sanguinalis) | Lambsquarter (Chenopodium) | Pigweed (Amaranthus retroflexus) | Mustard (Brassica arvensis) | Bermudagrass (Cynodon dactylon) | Switchgrass (Panicum virgatum) | Cheatgrass (Bromus secalinus) | Ryegrass Foxtail (Setaria glauca) | (Lolium multiflorum) |
|---|---|---|---|---|---|---|---|---|---|---|---|---|---|
| 1 | (1) | 3.7 | 100 | 92 | 99 | 100 | 100 | 100 | 97 | 85 | 63 | 100 | 80 |
| 2 | (2) | 3.7 | 78 | 78 | 95 | 90 | 100 | 98 | 100 | — | 100 | — | 100 |
| 3 | (3) | 3.7 | 100 | 99 | 87 | 100 | 100 | 100 | 92 | 100 | 63 | 100 | 99 |
| 4 | (4) | 3.7 | 100 | 100 | 88 | — | 98 | 100 | 98 | — | 70 | 100 | 87 |
| 5 | (5) | 3.7 | 100 | 99 | 100 | 100 | 100 | 98 | 88 | — | — | 100 | 96 |
| 6 | (6) | 3.7 | 82 | 83 | 97 | 82 | 100 | 98 | 80 | — | 3 | 99 | 80 |
| 7 | (7) | 11 | 97 | 87 | 97 | 85 | 100 | 98 | 100 | — | 80 | 100 | 97 |

| No. | $R^4$ | Conc | Sheep Sorrel (Rumex acetosella) | Bindweed (Convolvulus arvensis) | Vetch (Vicia sativa) | Plantain (Plantago lanceolata) | Curly Dock (Rumex crispus) | Dandelion (Taraxacum officinale) | WEEDS AVERAGE | Corn (Zea mays) | Wheat (Triticum aestivum) | Oats (Sierra) | Sorghum (Sorghum vulgare) | Rice (Calrose) | CROPS AVERAGE |
|---|---|---|---|---|---|---|---|---|---|---|---|---|---|---|---|
| 1 | (1) | 3.7 | 85 | 90 | 40 | 47 | 73 | 90 | 85 | 15 | 30 | 33 | 62 | 33 | 35 |
| 2 | (2) | 3.7 | 100 | 100 | 100 | 93 | 100 | 100 | 95 | 68 | 100 | 100 | 100 | 92 | 92 |
| 3 | (3) | 3.7 | 98 | 98 | 70 | 95 | 98 | 100 | 94 | 68 | 98 | 100 | 77 | 82 | 85 |
| 4 | (4) | 3.7 | 100 | 100 | 73 | 63 | 95 | 99 | 91 | 50 | 60 | 75 | 92 | 57 | 67 |
| 5 | (5) | 3.7 | 100 | 68 | 17 | 13 | 99 | 90 | 85 | 17 | 43 | 100 | 43 | 47 | 50 |
| 6 | (6) | 3.7 | 90 | 87 | 37 | 75 | 99 | — | 79 | 7 | 53 | — | 82 | 78 | 55 |
| 7 | (7) | 11 | 97 | 90 | 78 | 63 | 99 | — | 91 | 23 | 82 | — | 83 | 93 | 70 |

TABLE I-continued

Pre-Emergence (1)
(2) H
(3) —SSCH₃
(4) —ssн₂CH₂CH₃
(5) —ssΦ—4-cl
(6) —ssΦ
(7) —ssΦ-4-t-C₄H₉
[Φ = phenyl]

TABLE II

Post-Emergence

| No. | R⁴ | Conc | Wild Oats (Avena fatua) | Water-grass (Echinochola crusgalli) | Crabgrass (Digitaria sanguinalis) | Lambs quarter (Chenopodium) | Pigweed (Amaranthus retroflexus) | Mustard (Brasssica arvensis) | WEEDS AVERAGE | Corn (Zea mays) | Wheat (Triticum aestivum) | Oats (Sierra) | Sorghum (Sorghum vulgare) | Rice (Calrose) | CROPS AVERAGE |
|---|---|---|---|---|---|---|---|---|---|---|---|---|---|---|---|
| 1 | (1) | 11 | 100 | 99 | 93 | 100 | 100 | 100 | 99 | 7 | 7 | 40 | 23 | 12 | 18 |
|   |     | 3.7 | 82 | 95 | 35 | 98 | 95 | 100 | 84 | 0 | 5 | 5 | 7 | 0 | 3 |
| 2 | (2) | 11 | 100 | 90 | 100 | 100 | 100 | 100 | 98 | 75 | 100 | — | 100 | 100 | 44 |
|   |     | 3.7 | 100 | 72 | 58 | 100 | 98 | 100 | 88 | 15 | 70 | — | 55 | 32 | 43 |
|   |     | 1.2 | 80 | 47 | 12 | 100 | 7 | 100 | 58 | 5 | 7 | — | 12 | 15 | 10 |
| 3 | (3) | 11 | 100 | 88 | 20 | 96 | 80 | 100 | 81 | 93 | 57 | — | — | 52 | 67 |
|   |     | 3.7 | 47 | 30 | 0 | 80 | 53 | 75 | 48 | 27 | 25 | — | — | 40 | 31 |
| 5 | (4) | 11 | 100 | 100 | 100 | 100 | 100 | 100 | 100 | 100 | 67 | 85 | 83 | 93 | 86 |
|   |     | 3.7 | 100 | 73 | 85 | 100 | 98 | 100 | 93 | 32 | 15 | 15 | 28 | 33 | 25 |
| 6 | (5) | 11 | 100 | 100 | 100 | 85 | 100 | — | 97 | 72 | 95 | 87 | 75 | 37 | 73 |
|   |     | 3.7 | 52 | 57 | 3 | 100 | 73 | — | 57 | 8 | 68 | 15 | 3 | 0 | 19 |

(1) –S S– 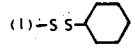

(2) H
(3) —SSCH₃
(4) —ssΦ-4-cl
(5) —ssΦ
[Φ = phenyl]

Pre- and post-emergent herbicidal field tests showing the use of N-methyl-N-cyclohexyldithio-N'-2-fluorophenyl urea for the selective elimination of grassy and broadleaf weeds from crop plants were made using the following methods:

Pre-Emergent Field Test

An emulsive concentrate of the test compound was prepared by blending 47.7 weight percent of the test compound, 42.8 weight percent of xylene, 6 weight percent of an anionic/nonionic surfactant blend, 2 weight percent of epoxized soybean oil, and 0.5 weight percent 4-methyl-2,6-di-t-butylphenol.

Seeds of the test vegetation were planted in 40 inches × 83 feet plots of loam soil fertilized with 100 lbs N, 26 lbs P₂O₅ and 26 lbs K₂O per acre. One to two days after planting, the soil was sprayed at a rate of 1 lb per acre with the emulsive concentrate of test solution. The soil plots were watered intermittently by irrigation or rainfall for a 30-day period and observed for seedling emergence, health of emerging seedlings, etc. At the end of this period, the herbicidal effectiveness of the compound was rated based on the physiological observations. A 0-to-10 scale was used, 0 representing no control and 10 representing complete kill. The results based on the average of 3 test plots per vegetation type appear in Table III.

Post-Emergent Field Test

The test compound was formulated and the seeds of the test vegetation were planted in the same manner described above for the pre-emergent field test.

Twenty days after planting, the emerging seedlings were sprayed at a rate of 1 lb per acre with the emulsive concentrate of test solution. The soil plots were watered intermittently by irrigation or rainfall during the test, and the seedlings were observed periodically for phytotoxic effects and physiological and morphological responses to the spray treatment. Fifteen days after treatment, the herbicidal effectiveness of the test compound was rated based on these observations. A 0-to-10 scale was used, 0 representing no phytotoxicity and 10 representing complete kill. The results based on the average of 3 test plots per vegetation type appears in Table III.

TABLE III

| Herbicidal Effectiveness | |
|---|---|
|  | Pre/Post |
| Weed Species |  |
| Velvet Leaf (Abutilon theophrasti) | 5.6/9.6 |
| Wild Oats (Avenua fatua) | 10/9.6 |
| Pigweed (Amaranthus retroflexus) | 10/9 |
| Prickly Sida (Sida spinosa) | 9.6/10 |
| Morning Glory (Ipomoea spp.) | 10.9 |
| Crop Species |  |
| Corn (Zea mays) | 0.6/0.3 |
| Sorghum (Sorghum bicolor) | 1.3/0 |
| Potato (Solanus tuberosum) | 1.0/0 |

What is claimed is:

1. N-methyl-N-cyclohexyldithio-N'-2-fluorophenyl urea.

* * * * *